United States Patent
Manzke et al.

(10) Patent No.: US 8,617,148 B2
(45) Date of Patent: Dec. 31, 2013

(54) TISSUE ABLATION DEVICE WITH PHOTOACOUSTIC LESION FORMATION FEEDBACK

(75) Inventors: Robert Manzke, Sleepy Hollow, NY (US); Raymond Chan, San Diego, CA (US); Ladislav Jankovic, Fishkill, NY (US); Daniel R. Elgort, New York, NY (US); Khalid Shahzad, Shrub Oak, NY (US)

(73) Assignee: Koninklijke Philips N.V., Eindhoven (NL)

( * ) Notice: Subject to any disclaimer, the term of this patent is extended or adjusted under 35 U.S.C. 154(b) by 317 days.

(21) Appl. No.: 12/810,043

(22) PCT Filed: Dec. 15, 2008

(86) PCT No.: PCT/IB2008/055312
§ 371 (c)(1),
(2), (4) Date: Jun. 22, 2010

(87) PCT Pub. No.: WO2009/083859
PCT Pub. Date: Jul. 9, 2009

(65) Prior Publication Data
US 2010/0280504 A1    Nov. 4, 2010

Related U.S. Application Data

(60) Provisional application No. 61/017,214, filed on Dec. 28, 2007.

(51) Int. Cl.
*A61B 18/18*    (2006.01)
*A61B 1/00*    (2006.01)
*A61B 19/00*    (2006.01)

(52) U.S. Cl.
USPC ........................ 606/11; 600/101; 128/898

(58) Field of Classification Search
USPC ................ 606/2–52; 600/101–183; 128/898
See application file for complete search history.

(56) References Cited

U.S. PATENT DOCUMENTS

| 7,238,178 B2 | 7/2007 | Maschke | |
| 2005/0119643 A1* | 6/2005 | Sobol et al. ................ | 606/9 |
| 2006/0055733 A1 | 3/2006 | Silverbrook | |

(Continued)

FOREIGN PATENT DOCUMENTS

| DE | 19916653 | 10/2000 |
| EP | 1953332 | 6/2008 |
| WO | WO0024315 | 5/2000 |
| WO | WO2007084981 | 7/2007 |

OTHER PUBLICATIONS

K.A. Roome, et al., "Towards a Sideways Looking Intravascular Laser-Ultrasound Probe", Sensors and Actuators 76 (1999) pp. 197-202.

(Continued)

*Primary Examiner* — Dawayne A Pinkney

(57) ABSTRACT

A tissue ablation device employs one or more energy emitters (21) and one or more photoacoustic sensors (22) in a cooperative arrangement for applying a tissue ablation therapy to a tissue (60). In operation, the energy emitters (21) emit a tissue ablation beam (TA) into a target portion of the tissue (60) to form a lesion (61) therein, and alternatively or concurrently emit a photoexcitation beam (PE) into the target portion of the tissue (60) to excite a photoacoustic response from the tissue (60). The photoacoustic sensor(s) (22) sense the photoacoustic response of the tissue (60).

15 Claims, 9 Drawing Sheets

(56) References Cited

U.S. PATENT DOCUMENTS

| | | |
|---|---|---|
| 2006/0122583 A1 | 6/2006 | Pesach et al. |
| 2008/0154257 A1* | 6/2008 | Sharareh et al. ............... 606/41 |
| 2008/0177138 A1* | 7/2008 | Courtney et al. ............ 600/109 |
| 2009/0093713 A1* | 4/2009 | Hyde et al. .................... 600/427 |
| 2010/0082019 A1* | 4/2010 | Neev ................................ 606/9 |

OTHER PUBLICATIONS

U. Oberheide et al., "Optoacoustic Online Control for Laser Cyclophotocoagulation", Biomedical Optoacoustics II, Proceed. of SPIE. vol. 4256 (2001), pp. 53-60.

* cited by examiner

TISSUE ABLATION DEVICE WITH PHOTOACOUSTIC LESION FORMATION FEEDBACK

CROSS-REFERENCE TO RELATED CASES

Applicants claim the benefit of International Application Number PCT/IB2008/055312, filed Dec. 15, 2008, and Provisional Application Ser. No. 61/017,214, filed Dec. 28, 2007.

The present invention generally relates to a tissue ablation device of any type for forming lesion in tissue. The present invention specifically relates to obtaining a photoacoustic lesion formation feedback from the tissue ablation device.

Atrial fibrillation ("AF") ablation is recognized as a growth opportunity for device and imaging vendors due to the increasing number of procedures. Tissue ablation device technologies based on cryo (freezing), laser and high intensity focused ultrasound ("HIFU") tissue destruction promise to simplify the placement of circumferential lesions, which are used to electrically isolate the pulmonary veinous ostia and thereby cure AF. However, methods for clinical monitoring and assessment of the lesion formation do not yet exist, precluding live feedback during the therapeutic procedure with regard to lesion size, depth and, hence, transmurality. To overcome this problem, the present invention provides a tissue ablation device which enables real-time assessment of ablation lesions using the photoacoustic effect. Specifically, this tissue ablation device ablates the cardiac tissue as known in the art and is equipped in accordance with the present invention with a photoacoustic response sensor which continuously monitors the acoustic tissue response and hence the ablation process.

One form of the present invention is a tissue ablation device comprising one or more energy emitters and one or more photoacoustic sensors in a cooperative arrangement for applying a tissue ablation therapy to a tissue. In operation, the energy emitter(s) emit a tissue ablation beam into a target portion of the tissue to form a lesion therein, and alternatively or concurrently emit a photoexcitation beam into the target portion of the tissue to excite a photoacoustic response from the tissue whereby the photoacoustic sensor(s) sense the photoacoustic response of the tissue.

A second form of the present invention is a system comprising a tissue ablation therapy control system and the aforementioned tissue ablation device. In operation, the tissue ablation therapy control system controls the emissions of the tissue ablation beam and the photoexcitation beam by the energy emitter(s), and monitors the formation of the lesion within the tissue based on the photoacoustic response of the tissue sensed by the photoacoustic sensor(s).

A third form of the present invention is a method of performing a tissue ablation therapy of a tissue. The method comprises an emission of a tissue ablation beam into the tissue wherein a lesion is formed in the tissue, an emission of a photoexcitation beam into the tissue wherein a photoacoustic response is generated within the tissue; and a sensing of the photoacoustic response of the tissue wherein a formation of the lesion in the tissue is monitored.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
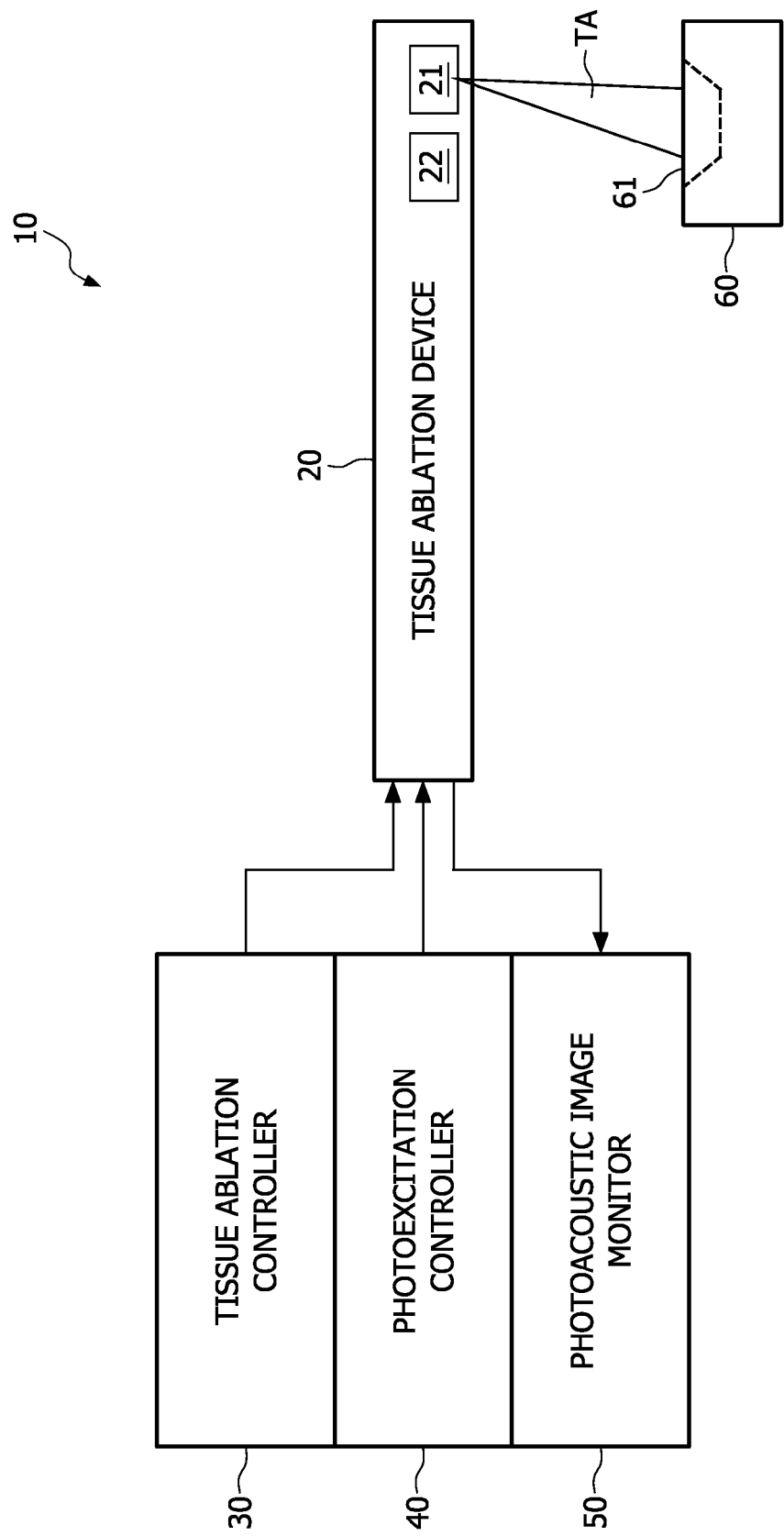
FIGS. 1 and 2 illustrate a block diagram of an embodiment of a tissue ablation system in accordance with the present invention.
Figure 2:
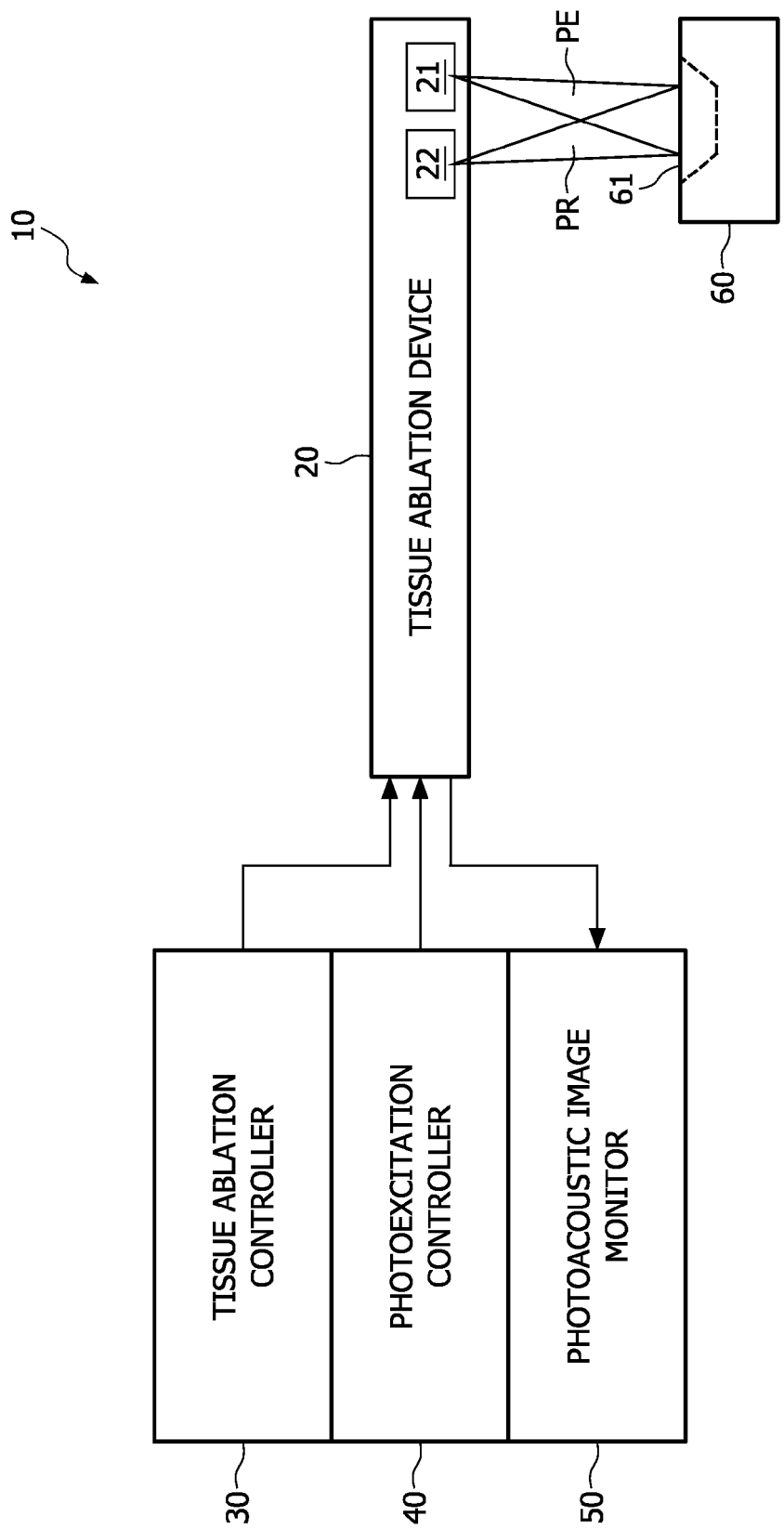

Referring to FIGS. 1 and 2, a tissue ablation system 10 of the present invention employs a tissue ablation device 20 having one or more energy emitters 21, and one or more photoacoustic sensors 22. Generally, one or more of the emitter(s) 21 of device 20 are driven by a laser ablation controller 30 for ablating a tissue 60. Alternatively or concurrently, one or more of the emitter(s) 21 of device 20 are driven by a photoexcitation controller 40 for generating a photoacoustic response by tissue 60. In turn, the photoacoustic sensor(s) 22 of device 20 sense such a photoacoustic response by tissue 60 and a photoacoustic monitor 50 generates a photoacoustic image of a lesion 61 being formed in tissue 60 based on the photoacoustic response as sensed by the photoacoustic sensor(s) 22 of device 20.

Figure 3:
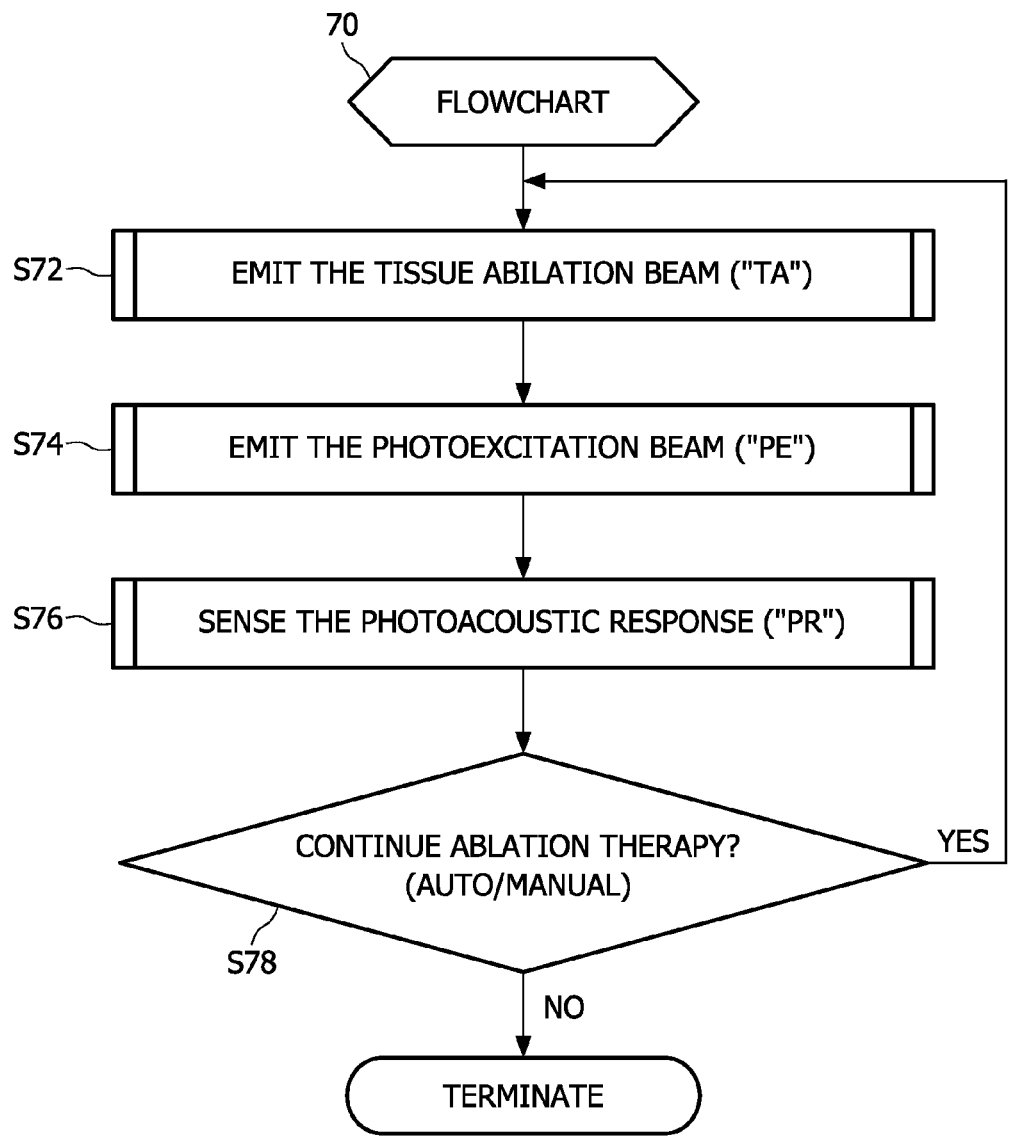
FIG. 3 illustrates a flowchart representative of a tissue ablation therapy method with photoacoustic lesion formation feedback in accordance with the present invention.

Specifically, tissue ablation system 10 implements a flowchart 70 as shown in FIG. 3 that is representative of a tissue ablation therapy method with photoacoustic lesion formation feedback in accordance with the present invention.

Referring to FIG. 3, a stage S72 of flowchart 70 encompasses laser ablation controller 30 driving one or more of the energy emitter(s) 21 of device 20 to emit a tissue ablation beam TA into a target portion of tissue 60 as best shown in FIG. 1. In practice, tissue ablation beam TA may be generated from any source (e.g., a laser, a RF source, or a high intensity ultrasound source), may be generated in any form (e.g., a single long pulse, a continuous wave beam or a series of short pulses), and may be modulated as needed.

A stage S74 of flowchart 70 encompasses photoexcitation controller 40 driving one or more of the emitter(s) 21 of device 20 to emit a photoexcitation beam PE into an ablated target portion of tissue 60 as best shown in FIG. 2. In practice, photoexcitation beam PE may be generated from any source (e.g., a laser, a RF source, or a high intensity ultrasound source), may be generated in any form (e.g., a single long pulse, a continuous wave beam or a series of short pulses), and may be modulated as needed. Further, tissue ablation beam TA and photoexcitation beam PE may be interleavingly or sequentially emitted by the same emitter(s) 21 of device 20 into the same target portion of tissue 60, or concurrently emitted by different emitters 21 of device 20 into different target portions of tissue 60 (e.g., one target portion of tissue 60 is ablated by tissue ablation beam TA while another previously ablated target portion of tissue 60 is being excited by photoexcitation beam PE).

A stage S76 of flowchart 70 encompasses the photoacoustic sensor(s) 22 of device 20 sensing a photoacoustic response PR by tissue 60 responsive to photoexcitation beam PE as known in the art. In practice, the photoacoustic sensor(s) 22 of device 20 may have any structural form (e.g., ultrasound piezo sensors, P-MUTS, C-MUts, Fabry-Perot optical interference or optical resonator based transducers).

A stage S78 of flowchart 70 encompasses photoacoustic monitor 50 generating a photoacoustic image of lesion 61 as formed in tissue 60 based on the sensed photoacoustic response PR of tissue 60 whereby the photoacoustic image is utilized to determine whether or not to continue with the ablation therapy of tissue 60. In one embodiment, the decision is an automated feature of monitor 50 whereby monitor 50 will terminate flowchart 70 upon the photoacoustic image indicating the lesion 61 has threshold features (e.g., a predetermined size and/or depth). In an alternative embodiment, the decision is a manual feature of monitor 50 whereby monitor 50 displays the photoacoustic image with a current listing of threshold features of lesion 61 to facilitate a user of system 10 in determining whether or not to terminate the ablation therapy of tissue 60.

Tissue ablation controller 30, photoexcitation controller 40 and photoacoustic image monitor 50 constitute a tissue ablation therapy control system. In practice, this system may have any structural configuration incorporating controller 30, controller 40 and monitor 50 as needed to control a tissue ablation device of the present invention.

To facilitate a further understanding of the present invention, a description of a balloon laser ablation device 120 (FIGS. 4-6) and a balloon laser ablation device 220 (FIGS. 7-9) will now be provided herein in the context of forming a circumferential lesion 63 within a tissue 61 (e.g., a pulmonary vein vessel tissue).

Figure 4:
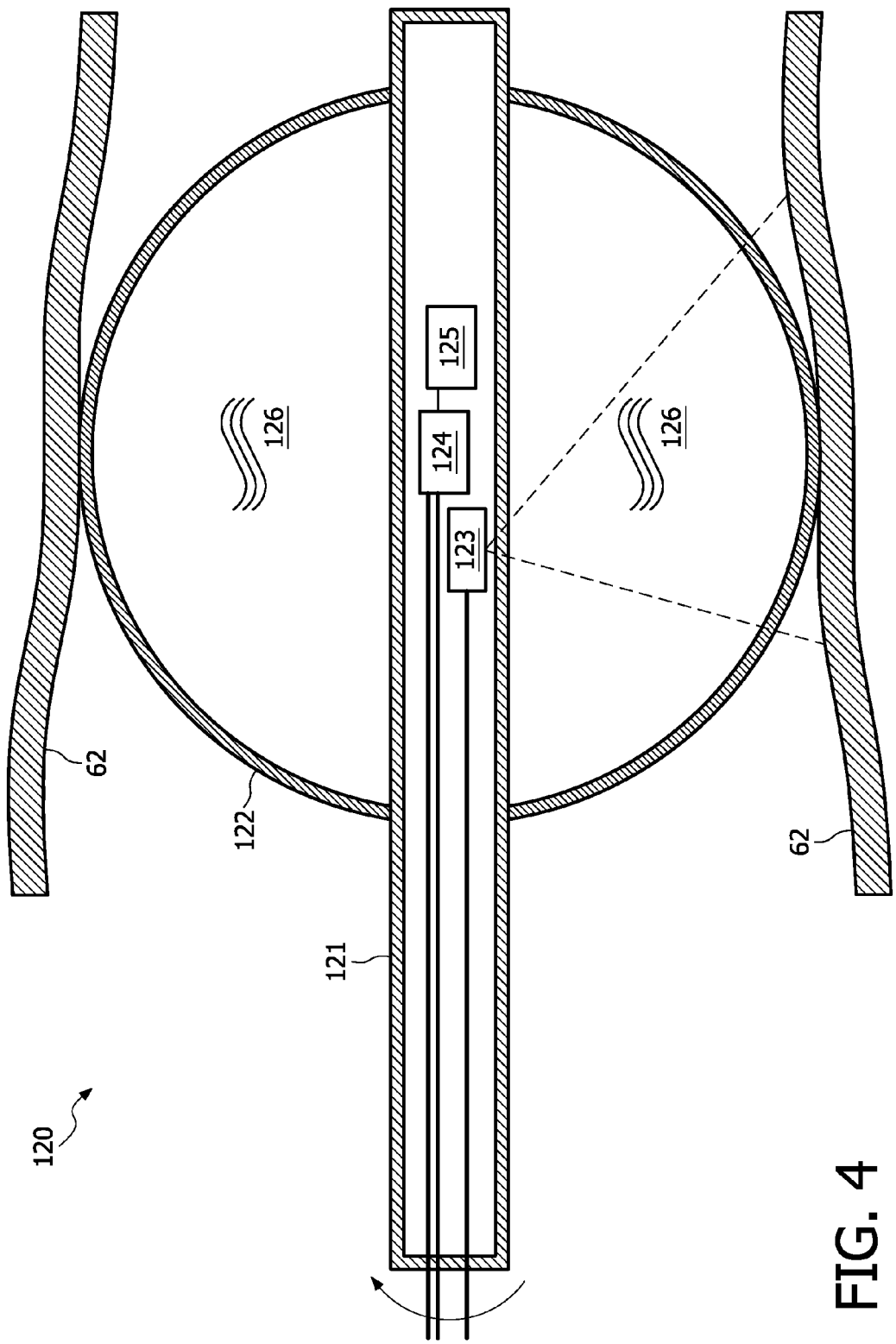
FIGS. 4-6 illustrate a first exemplary embodiment of a balloon laser ablation catheter in accordance with the present invention.
Figure 5:
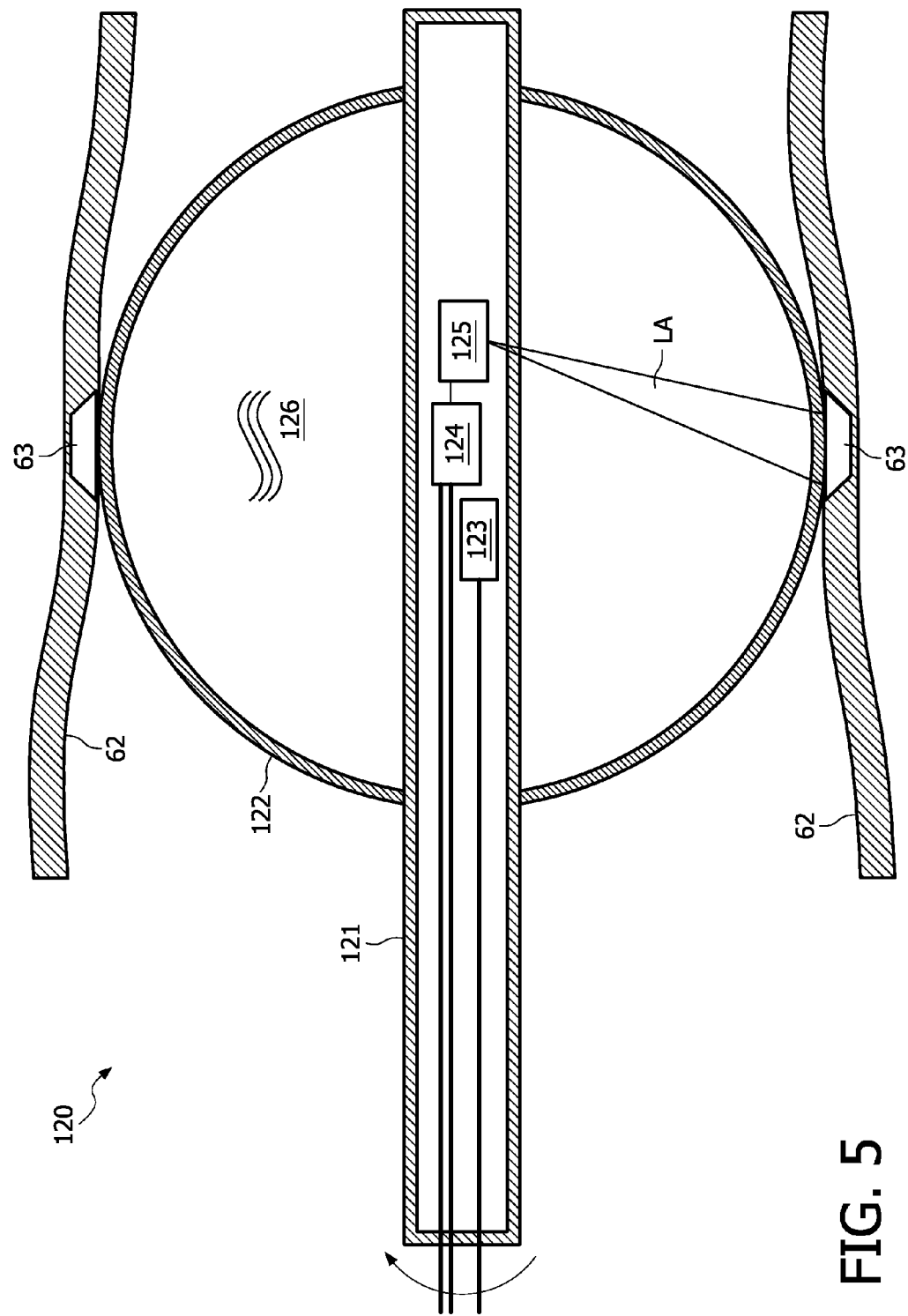
Figure 6:
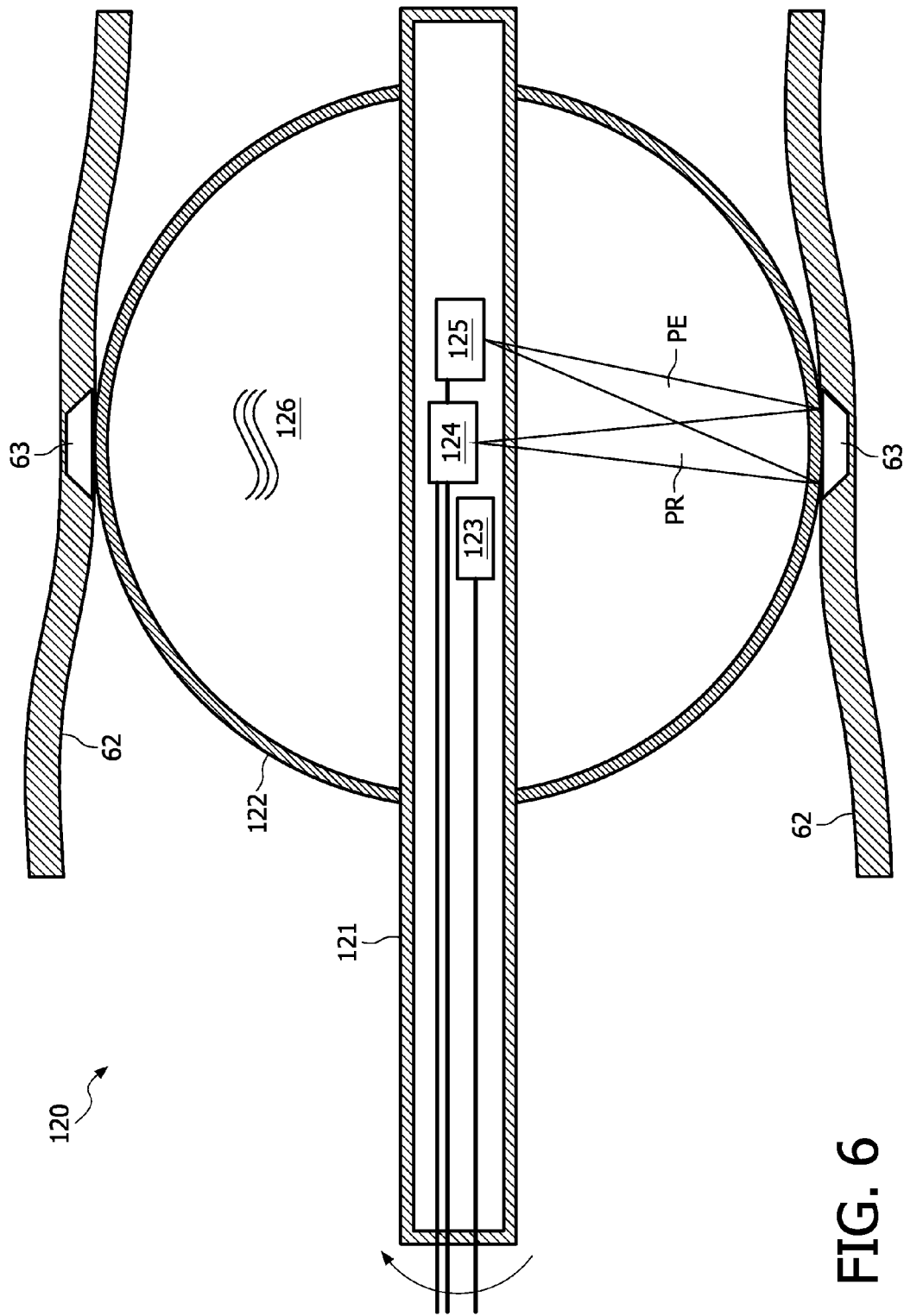

Referring to FIGS. 4-6, balloon laser ablation device 120 employs a catheter 121 having an inflatable balloon 122 affixed thereto and housing an endoscope 123, an ultrasound piezo sensor 124 and a laser emitter 125. To perform the laser ablation therapy, balloon 122 is filled with a suitable optoacoustic medium 126 which enables a laser beam from laser emitter 125 to travel to lesion 63 and enables ultrasound waves from tissue 62 to travel back to ultrasound piezo sensor 124. More particular, the material composition of balloon 122 and medium 126 may match that acoustic impedance of tissue 62 to facilitate an optimal signal propagation of a laser beam from laser emitter 125 to tissue 62 and of a photoacoustic response back to ultrasound piezo sensor 124 (e.g., a saline medium 126 filed within a latex balloon 122). In practice, medium 126 may be periodically flushed to maintain a constant temperature within balloon 122.

After the inflation of the balloon, a continual rotation of catheter 121 is started and endoscope 123 is used to locate a target portion of tissue 62 as best shown in FIG. 4. Upon locating the target portion of tissue 62, a laser ablation beam LA in the form of high energy light pulses or a high power continuous wave beam is emitted from laser emitter 125 through medium 126 to the target portion of tissue 62 to form lesion 63 in tissue 62 as best shown in FIG. 5. Interleaved with or subsequent to laser ablation beam LA, a photoexcitation beam PE in the form of a low-energy near-infrared laser pulses on the order of microseconds are used to illuminate tissue 62 to thereby induce a photoacoustic response PR sensed by ultrasound piezo sensor 124 as best shown in FIG. 6. In practice, laser ablation beam LA (FIG. 5) and photoexcitation beam PE (FIG. 6) may be deflected as needed to improve targeting of an ablation lesion 63 using electromechanically actuated lenses or mirrors.

Figure 7:
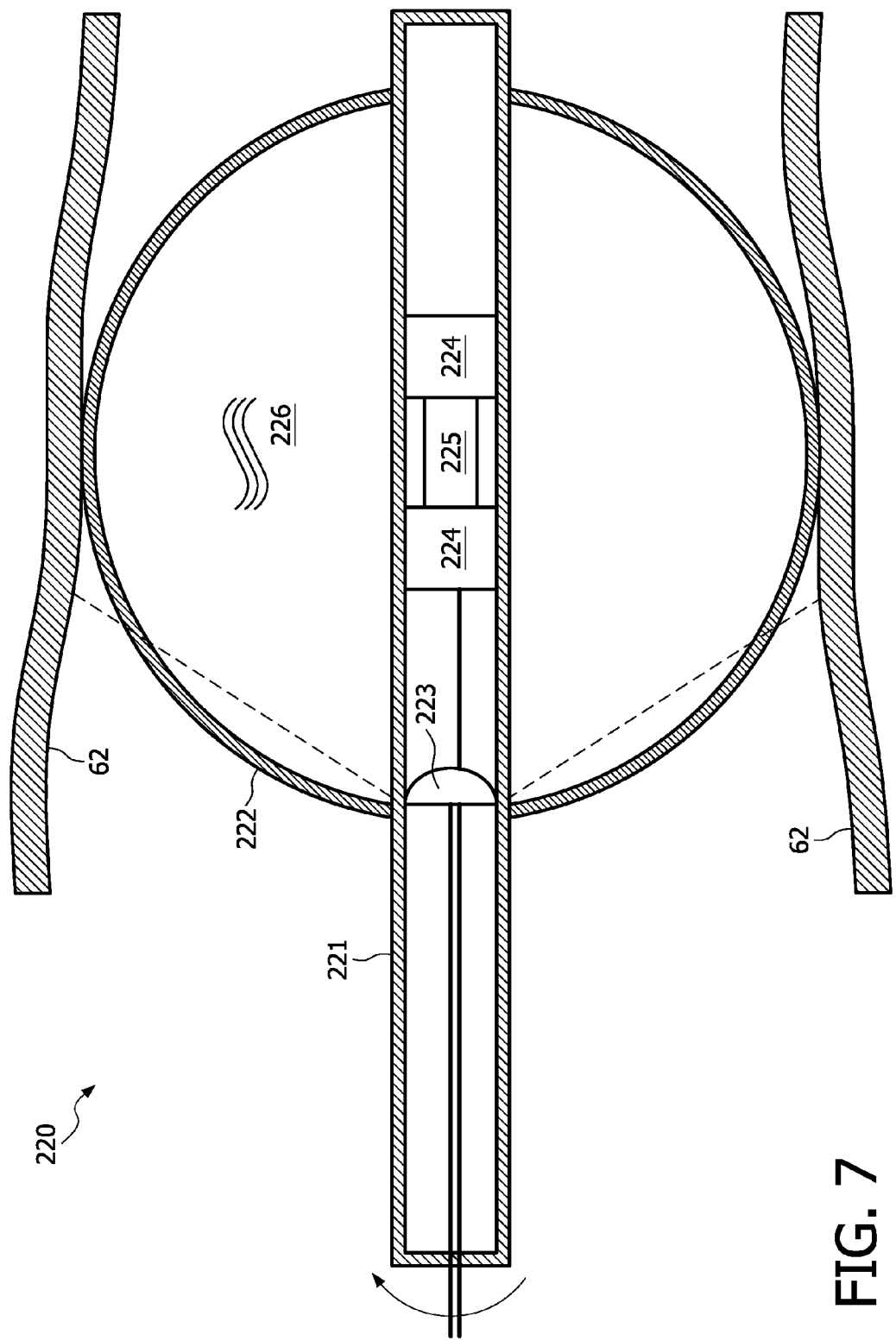
FIGS. 7-9 illustrate a second exemplary embodiment of a balloon laser ablation catheter in accordance with the present invention.
Figure 8:
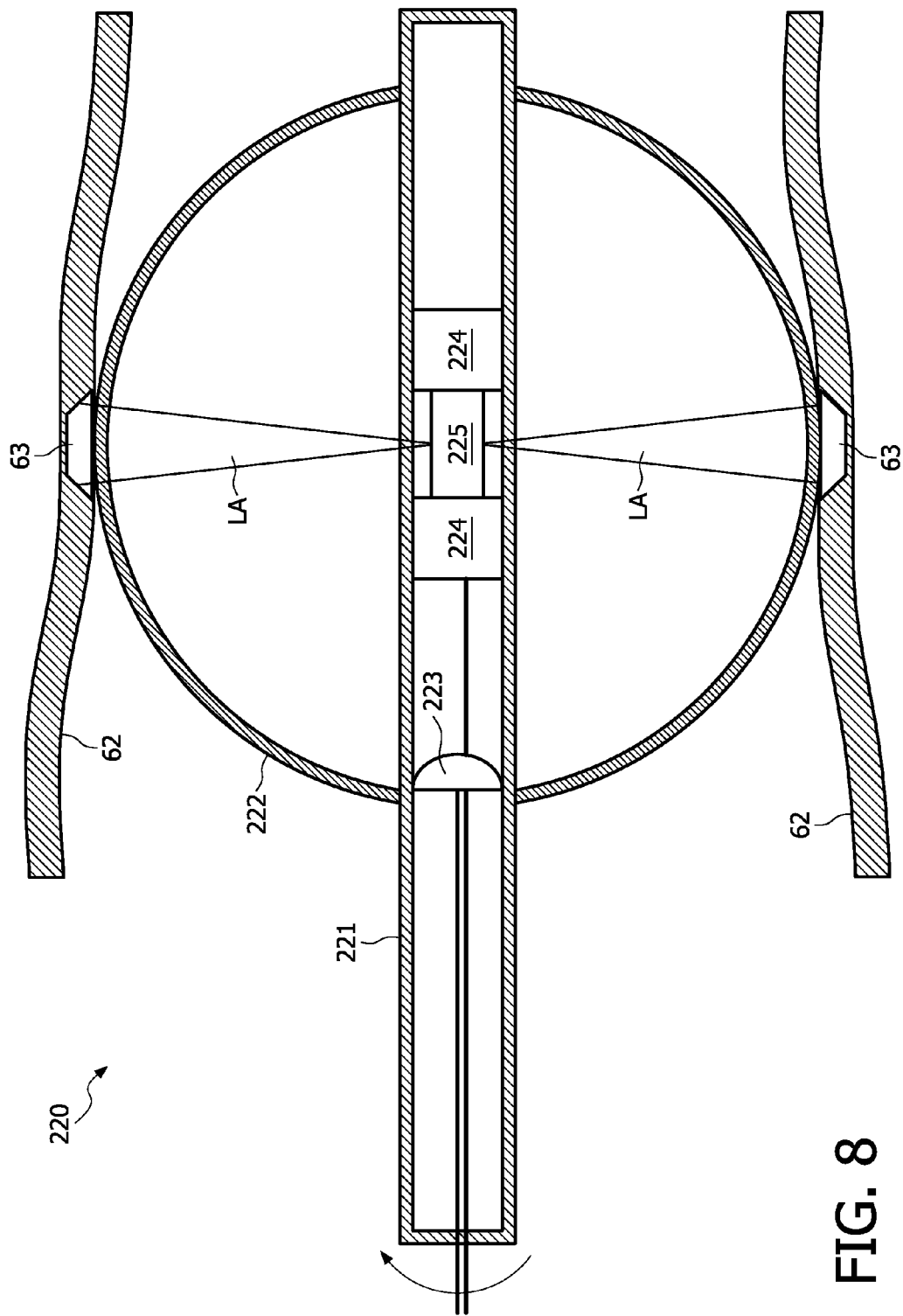
Figure 9:
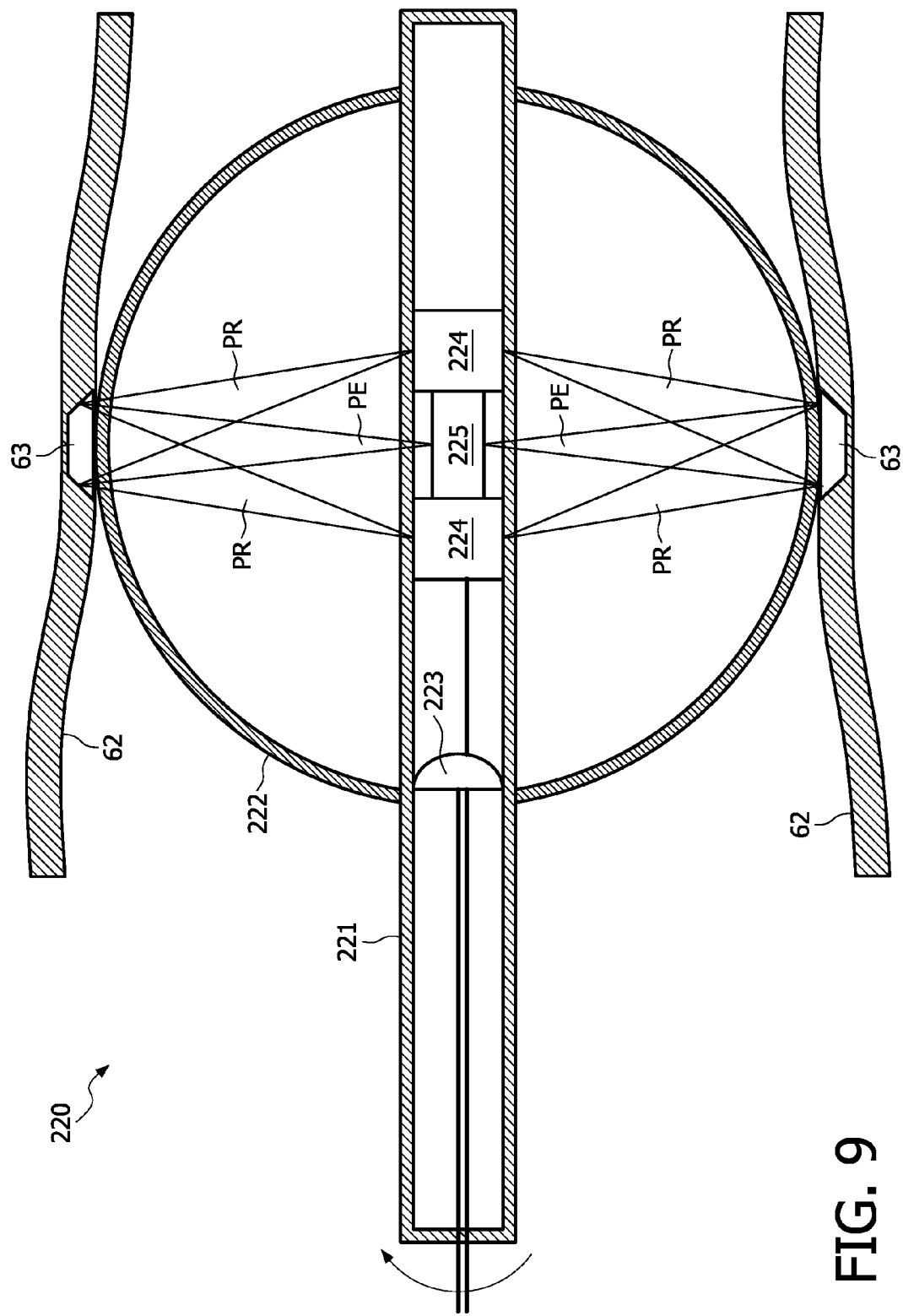

Referring to FIGS. 7-9, balloon laser ablation device 220 employs a catheter 221 having an inflatable balloon 222 affixed thereto and housing a fish-eye endoscope 223, a sensor arrays 224 having multiple ultrasound piezo elements, and a laser array 225 having multiple laser emitters. To perform the laser ablation therapy, balloon 222 is filled with a suitable optoacoustic medium 226 which enables a laser beam from laser array 225 to travel to lesion 63 and enables ultrasound waves from tissue 62 to travel back to sensor array 224. More particular, the material composition of balloon 222 and medium 226 may match that acoustic impedance of tissue 62 to facilitate an optimal signal propagation of a laser beam from laser array 225 to tissue 62 and of a photoacoustic response back to sensor array 224 (e.g., a saline medium 226 filed within a latex balloon 222). In practice, medium 226 may be periodically flushed to maintain a constant temperature within balloon 222.

After the inflation of the balloon, catheter 221 is held stationary and endoscope 223 is used to locate a target portion of tissue 62 as best shown in FIG. 7. Upon locating the target portion of tissue 62, a laser ablation beam LA in the form of high energy light pulses or a high power continuous wave beam is emitted from laser array 225 through medium 226 to the target portion of tissue 62 to form lesion 63 in tissue 62 as best shown in FIG. 8. Interleaved with or subsequent to laser ablation beam LA, a photoexcitation beam PE in the form of a low-energy near-infrared laser pulses on the order of microseconds are used to illuminate tissue 62 to thereby induce a photoacoustic response PR sensed by ultrasound piezo sensor array 224 as best shown in FIG. 9. In practice, laser ablation beam LA (FIG. 8) and photoexcitation beam PE (FIG. 9) may be deflected as needed to improve targeting of an ablation lesion 63 using electromechanically actuated lenses or mirrors.

In additional embodiments of a balloon laser ablation device of the present invention, a combination of rotating components (FIGS. 4-6) and stationary components (FIGS. 7-9) may be incorporated therein. For example, the laser emitter may be a static lens assembly which allows for beam refraction for focusing and reflection/deflection for steering, and the photoacoustic sensor may be rotated for purposes of photoacoustic imaging the lesion formed within the tissue. By further example, the laser emitter may be a rotating lens assembly which allows for beam refraction for focusing and reflection/deflection for steering, and the photoacoustic sensor may be static for purposes of photoacoustic imaging the lesion formed within the tissue.

Referring to FIG. 1-9, those having ordinary skill in the art will appreciate a tissue ablation device of the present invention can be utilized in numerous applications, and in practice, the actual structural configuration of a tissue ablation device of the present invention will be dependent upon the specifics of an explicit application of the device. Thus, the present invention does not contemplate any particular type of best structural configuration of a tissue ablation device in accordance with the present invention among the numerous potential applications.

Still referring to FIGS. 1-9, experiments have proven the photoacoustic imaging of a tissue lesion in accordance with the present invention can distinguish normal tissue over ablated tissue. For example, for a cardiac tissue including normal tissue and an ablated tissue formed from a full laser power of 123 mJ/cm$^2$ with a 800 nm laser, a scan over a lesion formation area of 22 mm×20 mm involving twenty (20) B-mode slices of the cardiac tissue at 1 mm separation in the scan direction shows the ablated tissue being visibly distinct from the normal tissue. A combination of the B-mode slices reconstructed a C-mode image of the lesion formation.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A tissue ablation device, comprising:
   at least one energy emitter (21) and at least one photoacoustic sensor (22) in a cooperative arrangement for applying a tissue ablation therapy to a tissue (60);
   wherein the at least one energy emitter (21) is operable to emit a tissue ablation beam (TA) into a target portion of the tissue (60) to form a lesion (61) therein;
   wherein the at least one energy emitter (21) is further operable to emit a photoexcitation beam (PE) into the target portion of the tissue (60) to excite a photoacoustic response from the tissue (60); and
   wherein the at least one photoacoustic sensor (22) is operable to sense the photoacoustic response of the tissue (60) to facilitate a generation of a photoacoustic image of the lesion (61) as formed in the tissue (60).

2. The tissue ablation device (20) of claim 1, further comprising:
   an endoscope (123, 223) for illuminating the target portion of the tissue (60).

3. The tissue ablation device (20) of claim 1, further comprising:
   a catheter (121, 221) housing the at least one energy emitter (21) and the at least one photoacoustic sensor (22); and
   an inflatable balloon (122, 222) affixed to the catheter (121, 221) and encircling the at least one energy emitter (21) and the at least one photoacoustic sensor (22),
      wherein the balloon (122, 222) is operable to be inflated via the catheter (121, 221) with an optoacoustic transfer medium (126, 226).

4. The tissue ablation device (20) of claim 1, wherein at least one of the at least one energy emitter (21) and the at least photoacoustic sensor (22) is rotated during the application of the tissue ablation therapy.

5. The tissue ablation device (20) of claim 1, wherein:
   the tissue (60) is a pulmonary vein vessel tissue; and
   the lesion (61) is a circumferential lesion formed within the pulmonary vein vessel tissue.

6. A tissue ablation system, comprising:
   a tissue ablation therapy control system; and
   a tissue ablation device (20) including:
      at least one energy emitter (21) and at least one photoacoustic sensor (22) in a cooperative arrangement for applying a tissue ablation therapy to a tissue (60);
      wherein the at least one energy emitter (21) is controllable by the tissue ablation therapy control system to emit a tissue ablation beam (TA) into a target portion of the tissue (60) to form a lesion (61) therein;
      wherein the at least one energy emitter (21) is further is controllable by the tissue ablation therapy control system to emit a photoexcitation beam into the target portion of the tissue (60) to excite a photoacoustic response from the tissue (60); and
      wherein the at least one photoacoustic sensor (22) is operable to sense the photoacoustic response of the tissue (60) to facilitate a generation of a photoacoustic image of the lesion (61) as formed in the tissue (60) by the tissue ablation therapy control system.

7. The tissue ablation system of claim 6, further comprising:
   an endoscope (123, 223) for illuminating the target portion of the tissue (60).

8. The tissue ablation system of claim 6, further comprising:
   a catheter (121, 221) housing the at least one energy emitter (21) and the at least one photoacoustic sensor (22); and
   an inflatable balloon (122, 222) affixed to the catheter (121, 221) and encircling the at least one energy emitter (21) and the at least one photoacoustic sensor (22),
      wherein the balloon (122, 222) is operable to be inflated via the catheter (121, 221) with an optoacoustic transfer medium (126, 226).

9. The tissue ablation system of claim 6, wherein at least one of the at least one energy emitter (21) and the at least photoacoustic sensor (22) are rotated during the application of the tissue ablation therapy.

10. The tissue ablation system of claim 6, wherein:
    the tissue (60) is a pulmonary vein vessel tissue; and
    the lesion (61) is a circumferential lesion formed within the pulmonary vein vessel tissue.

11. The tissue ablation system of claim 6, wherein the tissue ablation control system includes:
    a tissue ablation controller (30) operable to control an emission of the tissue ablation beam (TA) by the at least one emitter (21);
    a photoexcitation controller (40) operable to control an emission of the photoexcitation beam (PE) PE by the at least one emitter (21); and
    a photoacoustic image monitor (50) operable to monitor a formation of the lesion (61) within the tissue (60) based on the photoacoustic response of the tissue (60) as sensed by the at least one photoacoustic sensor.

12. A method of performing a tissue ablation therapy of a tissue (60), the method comprising:
    emitting a tissue ablation beam (TA) into the tissue (60), wherein a lesion (61) is formed in the tissue (60);
    emitting a photoexcitation beam (PE) into the tissue (60), wherein a photoacoustic response is generated within the tissue (60);
    sensing the photoacoustic response of the tissue (60); and
    generating and monitoring a photoacoustic image of the lesion (61) as formed in the tissue (60) in response to the sensing of the photoacoustic response of the tissue (60).

13. The method of claim 12, wherein the emissions of the tissue ablation beam (TA) and the photoexcitation beam (PE) are concurrent.

14. The method of claim 12, wherein the emissions of the tissue ablation beam (TA) and the photoexcitation beam (PE) are interleaved.

15. The method of claim 12, wherein the emissions of the tissue ablation beam (TA) and the photoexcitation beam (PE) are sequential.

* * * * *